United States Patent [19]

Prosen

[11] 4,179,288

[45] Dec. 18, 1979

[54] PALLADIUM BASE DENTAL ALLOY

[75] Inventor: Emil M. Prosen, Bala-Cynwyd, Pa.

[73] Assignee: Neoloy Products, Inc., Posen, Ill.

[21] Appl. No.: 6,078

[22] Filed: Jan. 24, 1979

[51] Int. Cl.$^2$ .............................................. C22C 5/02
[52] U.S. Cl. ................................. 75/172 G; 75/172 R
[58] Field of Search .............. 75/172 E, 172 G, 172 R

[56] References Cited

U.S. PATENT DOCUMENTS

| | | | |
|---|---|---|---|
| 3,134,671 | 5/1964 | Prosen | 75/172 |
| 3,137,571 | 6/1964 | Cooper | 75/172 |
| 4,012,228 | 3/1977 | Dudek et al. | 75/134 C |
| 4,124,382 | 11/1978 | Prosen | 75/172 R |

FOREIGN PATENT DOCUMENTS 2043492  3/1972  Fed. Rep. of Germany .............. 75/172

*Primary Examiner*—L. Dewayne Rutledge
*Assistant Examiner*—Upendra Roy
*Attorney, Agent, or Firm*—Cooper, Dunham, Clark, Griffin & Moran

[57] ABSTRACT

The present invention provides dental alloys which may be used in producing inlays, crowns and the like. It also provides alloys which are especially adapted for the application of low fusing porcelain for facings to improve the aesthetic appearance of the denture. The alloy of the present invention has a melting point around 2400° F. In its broadest aspect the alloy consists of gallium 7 to 12%, gold 2 to 5%, boron 0.125 to 0.50% and the balance palladium.

4 Claims, No Drawings

PALLADIUM BASE DENTAL ALLOY

The present invention relates to dental alloys, and more particularly to dental alloys which may be used in producing inlays, crowns and the like. The invention also relates to dental alloys which are especially adapted for the application of low fusing porcelain for facings to improve the aesthetic appearance of the denture.

It is well understood in the dental art that with the high price of gold and platinum, it is economically unsound to utilize these elements in substantial amounts if less costly elements can be substituted therefor.

One of the substitute elements which has been found to be highly desirable for use in dental appliances is palladium. Unfortunately, palladium has a melting point of about 2800° F. which makes it somewhat difficult to cast for dental appliances.

It is also well known that low fusing porcelain has a fusing temperature of about 1800° F. and that the metal alloy to which it is applied should have a minimum melting temperature of 2250° F. so as to maintain sufficient rigidity of the metal alloy during the porcelain application.

It is also well recognized that for porcelain application there should be provided on the surface of the metal alloy, oxides which contribute to the adhesion of the porcelain with the metal alloy.

Finally, it is well recognized that the coefficient of expansion and contraction of the metal alloy should be substantially the same as the coefficient of expansion and contraction of the low fusing porcelain, so as to avoid checks, cracks and fissures in the porcelain surface after cooling.

To my knowledge the following are the most pertinent U.S. patents relating to the subject matter of this application:
3,134,670
3,134,671
4,124,382 together with the references made of record during the prosecution of such patents.

In my opinion, none of the foregoing U.S. patents anticipate the invention herein disclosed and claimed; nor would it have been obvious to a man skilled in the art to evolve this invention from such prior art patents.

With all of the foregoing in mind, and after considerable experimentation and research, I have been able to produce a dental alloy consisting chiefly of palladium, and which contains relatively small amounts of other elements, which meets and satisfies all of the foregoing requirements.

The alloy which I have produced has a melting point around 2400° F. This alloy is not only practical for crowns and inlays, but is also practical for the application of low fusing porcelain.

In its broadest aspect the alloy consists of:
Gallium—7 to 12%
Gold—2 to 5%
Boron—0.125 to 0.50%
Palladium Balance I have also found that if I use 7% gallium, the gold should be 5%, and if I use 12% gallium, the gold should be 2%. In intermediate amounts, the gallium and gold would be correspondingly varied.

As earlier mentioned, palladium has a melting point of 2800° F. The reason for using a small amount of gold is that it has an eutectic effect, that is, it reduces the melting point of the palladium.

In proper proportions the combination of boron, gold and gallium can reduce the melting temperature of palladium to approximately 1800° F. An alloy melting at this temperature is useful in dentistry, but is not suitable for porcelain application.

For porcelain application the preferred melting temperature of the alloy should be approximately 2400° F. which is well above the well understood temperature of 2250° F. for low fusing porcelain application; and it is also well below the melting point of palladium as such, which is approximately 2800° F. and is very difficult to cast and work in dental applications.

In its preferred form the alloy of the present invention should consist of:
Gallium—8%
Gold—2%
Boron—0.125%
Palladium—Balance This alloy has a melting temperature of approximately 2400° F. and is ideally suited for the application of low fusing porcelain and has sufficient rigidity so as not to soften during porcelain application.

In addition, this alloy, consisting of gallium, gold, boron and palladium, when cast, forms on its surface an ideal oxide which facilitates the retention of low fusing porcelain to such alloy.

It is well understood in the art that porcelain will not fuse with metal unless it has an oxide of the metal to which to adhere. Pure gold will not oxidize and porcelain will not adhere to it. While palladium does oxidize to a certain extent, it does not provide sufficient oxide for the adhesion of porcelain. I have found, however, that with the alloying of gold, gallium and boron with palladium in the proportions set forth, an ideal oxide surface is provided for the fusion of porcelain thereto, and that such adhesion between the porcelain and the base alloy is stronger than the porcelain. In fact, the porcelain will not separate from the alloy when subjected to repeated hammer blows, but will merely fragment on its outer surface, while the inner surface remains intact with the alloy base metal.

As before mentioned, the preferred melting temperature for the alloy of the present invention is approximately 2400° F. By varying the elements within the ranges earlier set forth, the temperature can be as low as 2375° F. or as high as 2550° F. As also earlier mentioned, the low fusing porcelain temperature is preferably 1800° F. This porcelain temperature may also range from 1750° F. to 1850° F. without deleterious effects.

As earlier set forth, it is very important that the linear expansion of the metal be completely compatible with the linear expansion of the porcelain. It has been found by experimentation that the linear expansion of the alloy herein disclosed is substantially the equivalent of the linear expansion of the porcelain which not only renders them compatible, but eliminates the formation of checks, cracks and fissures in the porcelain upon cooling after fusing to the alloy.

What I claim is:
1. A dental alloy consisting essentially of:
Gallium—7% to 12%
Gold—2% to 5%
Boron—0.125% to 0.50%

Palladium—Balance

2. A dental alloy especially adapted for the adhesion of porcelain having a fusing temperature of 1750° F. to 1850° F., consisting essentially of:
Gallium—7% to 12%
Gold—2% to 5%
Boron—0.125% to 0.50%
Palladium—Balance
said alloy having a melting temperature of 2375° F. to 2550° F.

3. A dental alloy having a melting temperature of approximately 2400° F. and consisting essentially of:
Gallium—8%
Gold—2%
Boron—0.125%
Palladium—Balance 4. A dental alloy especially adapted to have porcelain fused thereto at approximately 1800° F., said alloy consisting essentially of:
Gallium—8%
Gold—2%
Boron—0.125%
Palladium—Balance
said alloy having a melting temperature of approximately 2400° F.